United States Patent [19]

Chester et al.

[11] Patent Number: 5,429,229
[45] Date of Patent: Jul. 4, 1995

[54] PACKAGED DENTAL ARTICLE

[75] Inventors: Bruce E. Chester, Irvine; Kenneth E. Hoevel, Monrovia, both of Calif.; Dwight W. Jacobs, River Falls, Wis.; Lawrence G. Brusby, Glendora; Evangelos G. Georgakis, Altaloma, both of Calif.

[73] Assignee: Minnesota Mining and Manufacturing Company, St. Paul, Minn.

[21] Appl. No.: 226,294

[22] Filed: Apr. 11, 1994

Related U.S. Application Data

[60] Division of Ser. No. 52,334, Apr. 22, 1993, Pat. No. 5,328,363, which is a continuation of Ser. No. 826,225, Jan. 21, 1992, abandoned, which is a continuation-in-part of Ser. No. 740,003, Aug. 2, 1991, abandoned.

[51] Int. Cl.[6] ............................................. B65D 85/00
[52] U.S. Cl. ................................... 206/63.5; 206/462
[58] Field of Search .................... 206/63.5, 363–370, 206/438, 461, 462, 463, 562, 563, 564; 433/9

[56] References Cited

U.S. PATENT DOCUMENTS

| 2,931,493 | 4/1960 | Pfohl | 206/462 |
|---|---|---|---|
| 2,931,494 | 4/1960 | Pfohl | 206/462 |
| 3,111,220 | 11/1963 | Bostrom | 206/462 |
| 3,144,343 | 8/1964 | Fritsche | 206/463 |
| 3,246,747 | 4/1966 | Blish | 206/462 |
| 3,250,003 | 5/1966 | Collito | 32/14 |
| 3,509,991 | 5/1970 | Hurst | 206/59 |
| 4,204,325 | 5/1980 | Kaelble | 433/9 |
| 4,211,021 | 7/1980 | Amprim et al. | 40/2 R |
| 4,903,840 | 2/1990 | So | 206/581 |
| 4,948,367 | 8/1990 | Haas | 433/9 |
| 4,954,080 | 9/1990 | Kelly et al. | 433/8 |
| 4,978,007 | 12/1990 | Jacobs et al. | 206/469 |
| 4,979,611 | 12/1990 | Bolliger et al. | 206/83 |
| 5,015,180 | 5/1991 | Randklev | 433/9 |
| 5,100,320 | 3/1992 | Martin et al. | 433/90 |
| 5,172,809 | 12/1992 | Jacobs et al. | 206/368 |
| 5,183,403 | 2/1993 | Masuhara et al. | 433/9 |
| 5,221,202 | 6/1993 | James | 433/9 |

FOREIGN PATENT DOCUMENTS

| 3733524 | 5/1989 | Germany | 206/369 |
|---|---|---|---|
| PCT/JP89/0-1109 | 5/1991 | Japan | |
| 92/08419 | 5/1992 | WIPO | 433/9 |

Primary Examiner—Jimmy G. Foster
Attorney, Agent, or Firm—Gary L. Griswold; Walter N. Kirn; James D. Christoff

[57] ABSTRACT

A packaged dental article includes a dental appliance that is precoated with an adhesive. The adhesive is in contact with a flexible film having a low adhesion surface. The film is secured to a container at a location spaced from the appliance so that the film tends to peel away from the adhesive when the appliance is removed from the container in order to inhibit separation of the adhesive from the appliance. The container has a sidewall with a recess that engages a carrier to hold the container, and the carrier is flexible to permit the container to be inserted into or released from the carrier when desired.

7 Claims, 4 Drawing Sheets

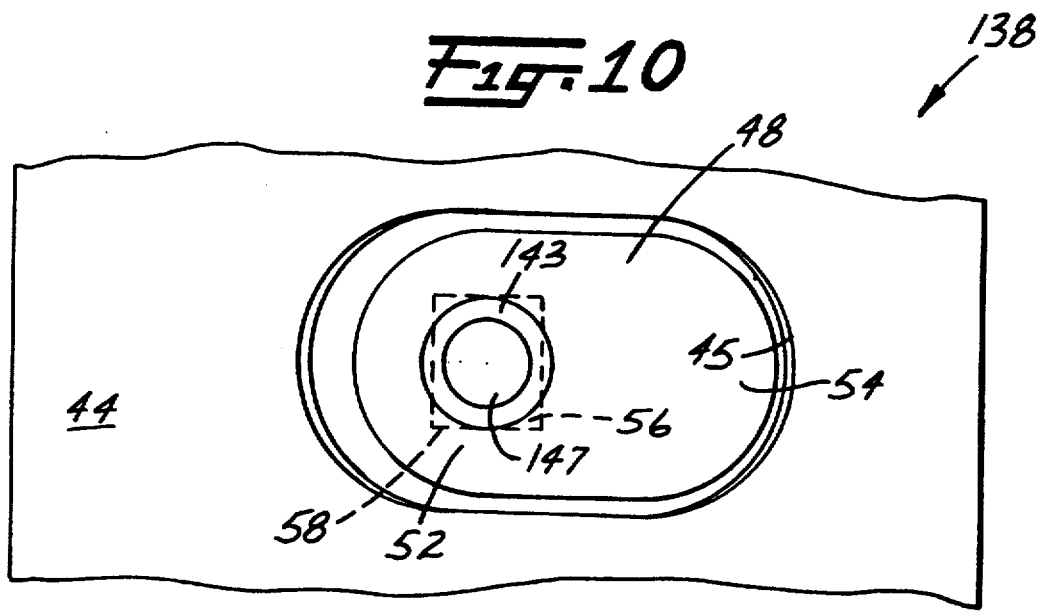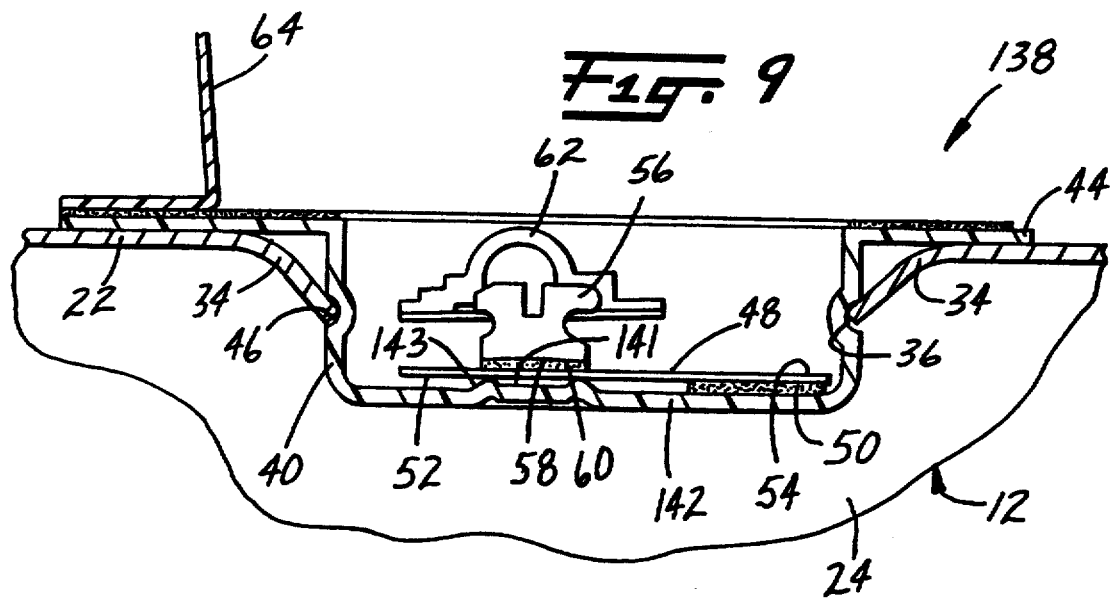

PACKAGED DENTAL ARTICLE

This is a division of application Ser. No. 08/052,334 filed Apr. 22, 1993, Pat. No. 5,328,363, which is a continuation of U.S. patent application Ser. No. 07/826,225, filed Jan. 21, 1992, abandoned, which is a continuation-in-part of U.S. patent application Ser. No. 07/740,003, filed Aug. 2, 1991, abandoned.

BACKGROUND OF THE INVENTION

1. Field of the Invention

This invention relates to a packaged dental article that is precoated with adhesive for direct bonding to a tooth surface.

2. Description of the Related Art

Orthodontic treatment concerns movement of malpositioned teeth to orthodontically correct positions. During treatment, tiny brackets are often connected to the patient's teeth, and an archwire is then secured in a slot of the brackets. The brackets are urged along the archwire by bends or twists in the archwire or by elastic members or other means in order to shift the associated teeth to desired positions.

Previously, orthodontic brackets were connected to teeth by welding or brazing each bracket to a band which was then placed over a tooth in encircling relation. In more recent years, orthodontic brackets have been directly bonded to the tooth surface, resulting in a more aesthetic appearance. Light curable adhesives have been developed which allow the orthodontist to precisely position the bracket on the tooth and then activate a lamp to cure the adhesive and securely fix the bracket in place.

Recent advances in the field of direct bonded dental articles are described in U.S. Pat. Nos. 5,015,180 and 4,978,007, both of which are assigned to the assignee of the present invention. U.S. Pat. No. 5,015,180 describes in one embodiment an orthodontic bracket and a light curable paste sandwiched between a base of the bracket and a flexible, releasably adhering cover sheet. To bond the bracket to a tooth, the cover sheet is removed from the paste and the bracket base is then applied to the tooth. Such construction represents a time savings for the orthodontist, because the orthodontist need not dispense and apply the adhesive paste to the bracket base before bonding the bracket to the tooth.

U.S. Pat. No. 4,978,007 describes in one embodiment a substrate having a recess, an orthodontic bracket having an adhesive on an exterior surface, and a release coating sandwiched between the adhesive and an interior surface of the recess. Such construction is advantageous in that the adhesive is protected in the recess from light, oxygen, water vapor and contaminants. Also, the bracket may be retained in the recess in an upright manner that facilitates grasping of the sides of the bracket by a placement instrument or other tool in order to pull the bracket and adhesive away from the release coating.

Many orthodontists prefer to use certain adhesives that are less viscous (i.e., more fluid) than other adhesives. However, some adhesives with a relatively low viscosity have been found to occasionally distort in shape or remain on the release coating described in U.S. Pat. No. 4,978,007 as the bracket is lifted from the substrate, such that the orthodontist may need to pause to re-shape the adhesive or apply additional adhesive to the bracket base.

SUMMARY OF THE INVENTION

The present invention is directed toward an article that comprises a substrate, a dental appliance having an exterior surface, and an adhesive on the exterior surface. A flexible film has a first section and a second section spaced from the first section. The first section includes a low adhesion surface in contact with the adhesive. Means is provided for securing the second section to the substrate while the first section is substantially unsecured to the substrate, such that the first section is movable away from the substrate during release of the adhesive from the film.

As a result, the first section of the film typically undergoes a peeling motion relative to the adhesive as the appliance is lifted from the substrate, rather than moving in a direction perpendicularly away from the appliance in generally flatwise fashion. The peeling motion facilitates separation of the film from the adhesive and permits the use of adhesives that are less viscous and preferred by some orthodontists. Securing the second section of the film to the substrate obviates the need for separate handling of the film, so that the film and substrate can be disposed of together.

The invention also concerns a dental packaging assembly that comprises a carrier having edge structure defining a plurality of openings. A plurality of containers are received in respective openings. Each container has a sidewall and a bottom defining a well for receiving a dental article. At least one cover is provided for initially closing the well of each container. The sidewall of each container includes a recess in contact with the edge structure for retaining the container in the opening.

Additionally, the invention concerns a packaging assembly that comprises a container having a well, and a cover connected to the container. The cover includes a line of perforations to facilitate movement of the cover from a closed position to an open position relative to the container.

Another embodiment of the invention concerns an article comprising a substrate, a dental appliance having an exterior surface, and an adhesive on the exterior surface. A flexible film having a first section including a low adhesion surface is in contact with the adhesive, and the first section extends over a portion of the substrate. Means is provided for supporting the first section over the portion of the substrate in such an orientation that full face-to-face contact is avoided.

BRIEF DESCRIPTION OF THE DRAWINGS

FIG. 9 is a view somewhat similar to FIG. 7 according to another embodiment of the invention; and FIG. 10 is a fragmentary plan view of a container alone (with a cover removed) that is also shown in FIG. 9.

DESCRIPTION OF THE PREFERRED EMBODIMENT

Figure 1:
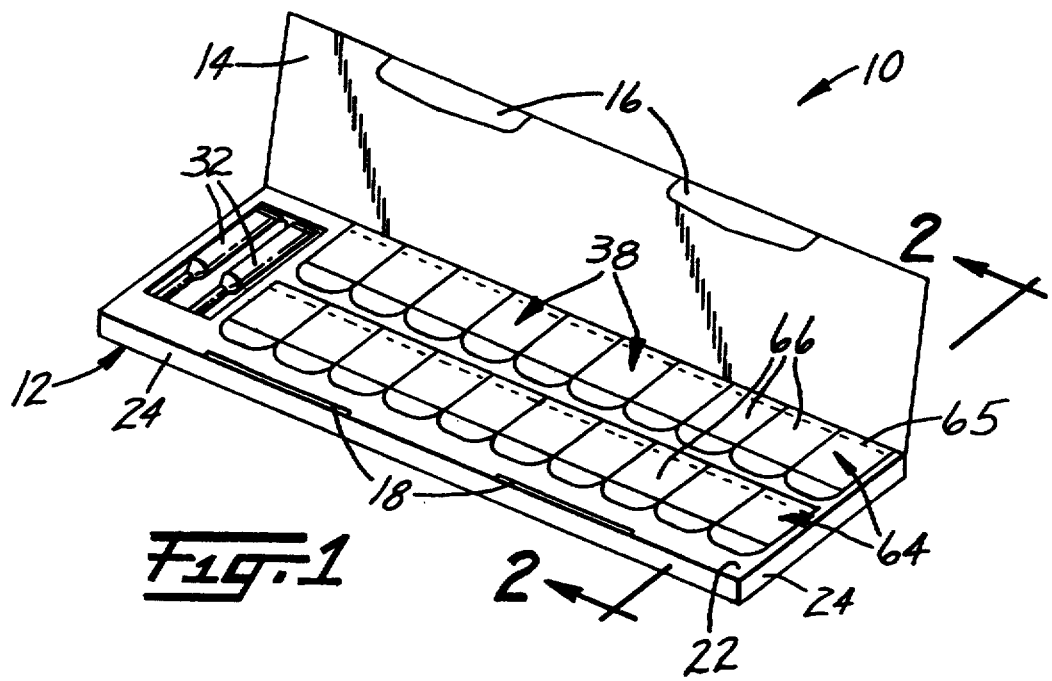
FIG. 1 is a perspective view of a dental packaging assembly in accordance with one embodiment of the invention.
Figure 2:
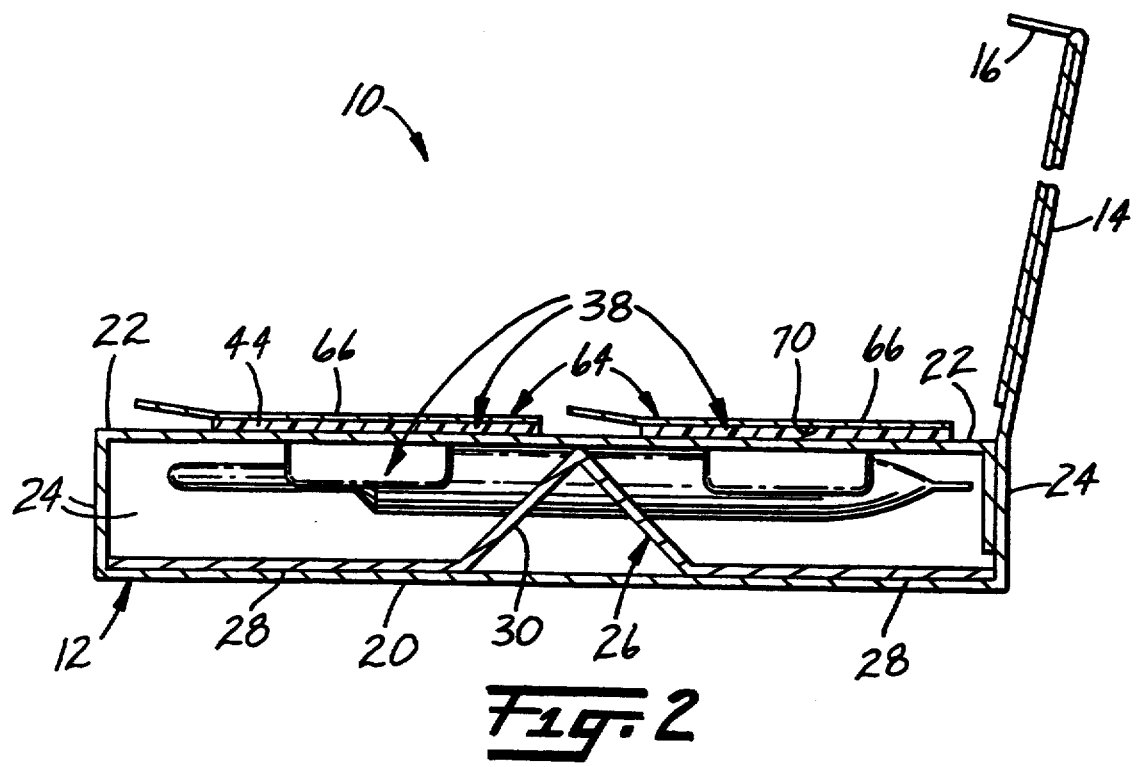
FIG. 2 is an enlarged side cross-sectional view of the assembly shown in FIG. 1.
Figure 3:
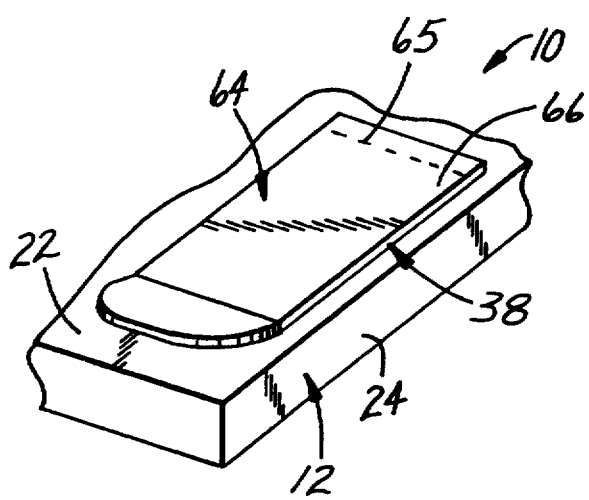
FIG. 3 is an enlarged, perspective, fragmentary view of one corner of the assembly shown in FIG. 1.
Figure 4:
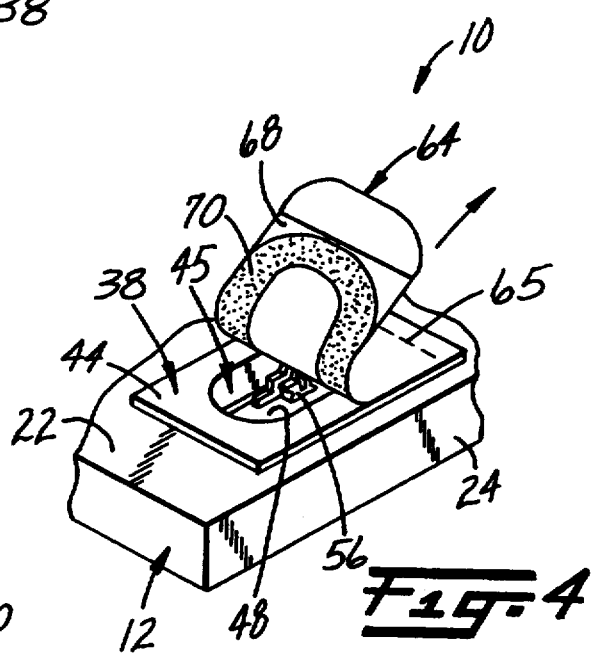
FIG. 4 is a view somewhat similar to FIG. 3 except that a cover of a container has been partially opened.

A dental packaging assembly 10 is illustrated in FIGS. 1–8, and includes a rectangular box 12 having a swingable, upper lid 14 that can be observed in FIGS. 1 and 2. A pair of tabs 16 are connected to the lid 14 and are received in respective front slots 18 (FIG. 1) in order to retain the lid 14 in a closed position when desired.

The box 12 includes a flat, rectangular bottom 20 and a flat, rectangular top carrier 22. The carrier 22 is interconnected with the bottom 20 by four upright walls 24 (including front and back walls and two end flap walls). As illustrated in FIG. 2, an insert 26 is received in the chamber between the bottom 20 and the carrier 22, and the insert 26 has elongated legs 28 that rest against the walls 24. A central arch 30 of the insert 26 extends along the length of the box 12 in contact with the carrier 22 in order to support a central portion of the carrier 22. The box 12 and the insert 26 are made of 0.4 mm thick clay coated solid bleached sulfate paperboard.

A left end portion (viewing FIG. 1) of the carrier has an aperture that overlies two applicator units 32 containing a swab predosed with an orthodontic adhesive primer. The units 32 are releasably received in notches formed in the arch 30 of the insert 26, and are somewhat similar to the assemblies described in U.S. Pat. No. 4,952,204, the disclosure of which is incorporated by reference herein.

The carrier 22 has edge structure 34 (FIGS. 7–8) that defines a plurality of oval-shaped openings 36 arranged in two rows. A container 38 is releasably received in each of the openings 36. Preferably, two rows of containers 38, each row containing ten containers 38, is provided to separately contain a dental appliance such as an orthodontic bracket for each tooth involved in treatment.

Each container 38 includes an upright sidewall 40 (see also FIGS. 7–8) that defines an oval in plan view. An oval-shaped bottom substrate 42 is integrally connected to the sidewall 40, and the substrate 42 and the sidewall 40 together define a well 45. The sidewall 40 is also connected to an oval-shaped central opening of a rectangular top flange 44. The sidewall 40 has two horizontally extending recesses 46 that engage the edge structure 34 of the carrier 22.

The container 38 is formed from a sheet of flexible material that provides a substantial barrier to the transmission of light. Preferably, the container 38 is black 0.33 mm thick polyethylene terephthalate glycol ("Kodar" brand PETG No. 6763, Kodak Chemical Company) that is treated with a silicone release agent (No. 24, Dow Chemical). The configuration of the opening 36 presents a slight interference fit with the sidewall 40 such that the edge structure 34 will slightly deform or deflect (see FIGS. 7–8) when the container 38 is inserted in the opening 36 of the carrier 22. Normally, the deflected edge structure 34 will thereafter retain the container 38 in the opening 36, although sufficient urging of the container 38 will permit removal of the container 38 from the opening 36 when desired.

A flexible film 48 having an oval configuration in plan view is received in the well 45 as shown in FIGS. 4–8. The film 48 is a 0.05 mm thick sheet of fluorinated ethylene propylene copolymer ("Teflon" brand FEP No. 200 C, clear, E.I. du Pont de Nemours & Company) that is etched on one side by electrostatic discharge apparatus to enhance the bond to an acrylic pressure sensitive adhesive 50 (No. V-29, Flexcon Company, Inc., Spencer, Mass.) that secures the film 48 to the substrate 42 of the well 45.

Figure 7:
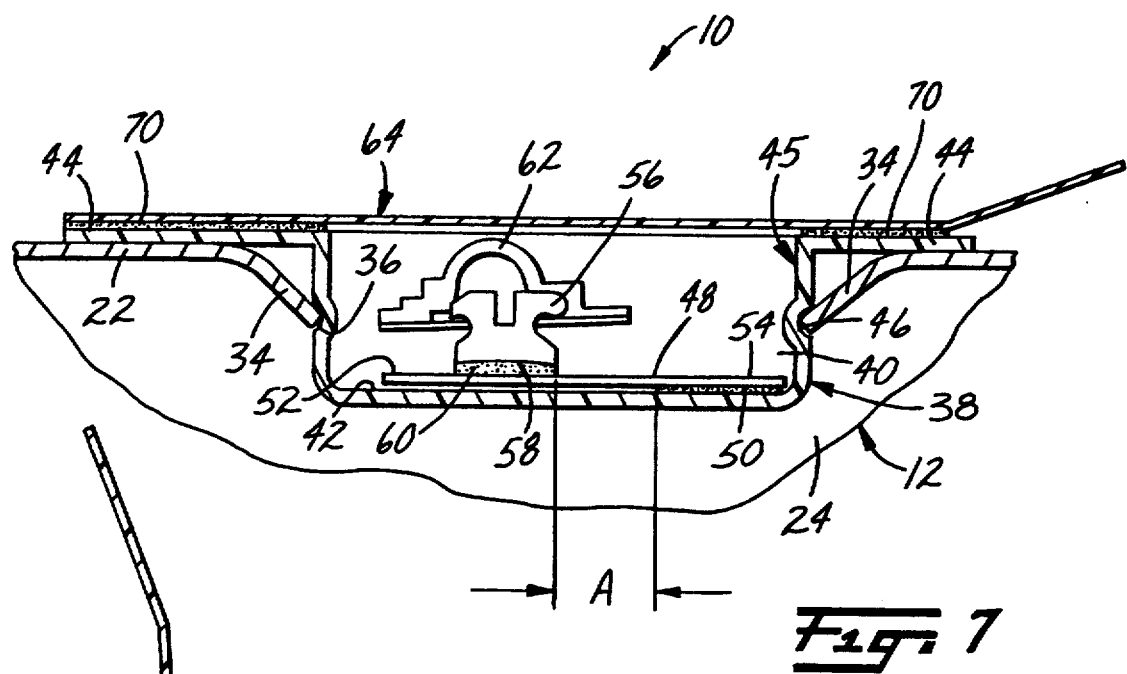
FIG. 7 is a side cross-sectional view of the container and cover shown in FIG. 3, also illustrating the bracket and flexible film in the well.
Figure 8:
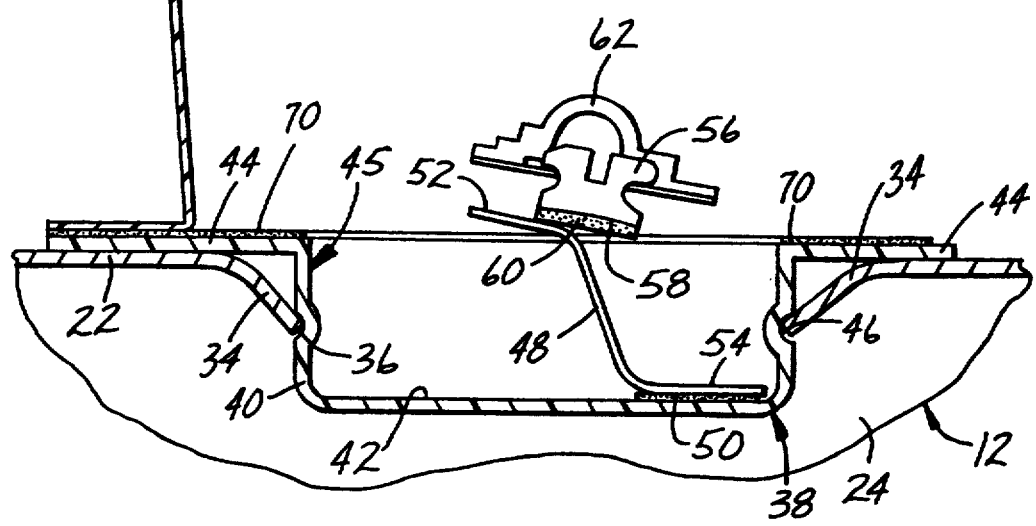
FIG. 8 is a view somewhat similar to FIG. 7 except that the cover has been opened and the bracket has been lifted from the well in similar fashion to the step shown in FIG. 5.

The film 48 has a first end section 52 that overlies a first portion of the substrate 42 on the left-hand side of the well 45 (viewing FIGS. 7–8). The pressure sensitive adhesive 50, however, only contacts a second end section 54 of the film 48 that overlies a second portion of the substrate 42 on the right-hand side of the well 45 viewing FIGS. 7–8. The second section 54 is laterally spaced from the first section 52 along the normal flat plane of the film 48 (i.e., is spaced in a horizontal direction viewing FIGS. 7–8). The first section 52 is free of pressure sensitive adhesive 50, and therefore is somewhat unrestrained and substantially free of direct connection to the substrate 42 of the well 45. The fluorinated ethylene propylene copolymer material provides a low adhesion surface for the film 48 including the surface of the first section 52 in contact with the adhesive.

An orthodontic appliance 56 is initially received in the well 45 and in the drawings comprises an orthodontic bracket made of a translucent ceramic material such as disclosed in U.S. Pat. No. 4,954,080. Alternatively, the appliance 56 could be made of other materials such as metal, glass or plastic, and could be in the form of an orthodontic buccal tube or other dental device adapted to be bonded to a tooth surface or other structure. As can be observed in FIGS. 7–8, the appliance 56 has an exterior base surface 58 having a concave, compound contour to match the contour of the tooth.

An adhesive 60 is received on the exterior surface 58 of the appliance 56 and preferably is a light-curable, non-toxic adhesive paste. Preferably the adhesive 60 is in releasable engagement with the first section 52 of the film 48 in FIGS. 4–5 and 7–8. The adhesive includes a resin system and a filler system, and the resin system includes both diglycidylmethacrylate of Bisphenol A ("Bis-GMA") and ethoxylated Bisphenol A dimethacrylate ("EBDMA"), along with a photoinitiator, a catalyst, an inhibitor and an amine. The EBDMA is preferably "DIACRYL 101" from Akzo Chemie America.

The amounts of the components used in the adhesive vary depending on the desired consistency of the paste. The weight ratio of Bis-GMA/EBDMA in the resin system can range from 5/95 to 80/20 with a preferred range being from 40/60 to 70/30 and a more preferred range being from 49/51 to 63/37. The amount of photoinitiator is generally sufficient to cure the resin after a brief exposure to a curing light (e.g., 10 to 15 seconds) and is generally in the range of 0.05–0.5 weight %. The amount of catalyst is preferably about 0.2–1.0 weight %. The amount of inhibitor is preferably in the range of 0.05 to 0.2 weight % and the amount of amine is preferably about 0.2–2.0 weight %. The paste preferably comprises about 14–30 weight % resin and 86–70 weight % filler. If quartz filler is used, the paste preferably comprises about 17–22 weight % resin and about 83–78 weight % filler and more preferably about 19.5–21 weight % resin and 80.5–79 weight % filler.

The dental adhesive of the present invention can also contain suitable adjuvants such as solvents, accelerators, absorbers, diluents, stabilizers, pigments, dyes, inorganic or organic fibrous or particulate reinforcing or extending fillers, viscosity modifiers, inhibitors, surface tension depressants, wetting aids, thixotropic agents, antioxidants, medicaments (e.g., leachable fluorides), and other ingredients well known to those skilled in the art.

The viscoelastic behavior of the adhesive is determined by a consistency measurement. Consistency is measured as the spread of 1.04 g±0.01 g of adhesive sandwiched between two 10.16×10.16 cm glass plates under a 907.2 g weight. The adhesive is delivered onto the bottom plate, then the top plate and the 907.2 g weight are added. The combined mass of the top plate and the 907.2 g weight is 1027±10 g. After two minutes, the spread (diameter) of the adhesive is measured to the nearest 0.8 mm, and three readings are averaged. The consistency is preferably in the range of about 12 mm to 28 mm, more preferably is in the range of about 21 mm to about 26 mm, and most preferably is in the range of about 23 mm to about 24.5 mm.

A long axis indicator 62 made of poly(acrylonitrilebutadiene-styrene) (ABS) is in releasable, snap-fit contact with a side of the appliance 56 opposite the exterior surface 58. The indicator 62 serves as a guide to align the appliance 56 with the long axis of the tooth as the appliance 56 is positioned on the tooth surface. Once the adhesive 60 has cured by exposure to actinic radiation to firmly fix the appliance 56 in place on the tooth, the indicator 62 is removed from the appliance 56.

Each of the containers 38 is provided with a cover 64 to initially close the well 45. The cover 64 provides a substantial barrier to the transmission of water vapor, light and oxygen to protect the light-sensitive adhesive 60. Various suitable materials for making the cover 64 are disclosed in pending U.S. patent application Ser. No. 07/615,702, filed Nov. 20, 1990, the disclosure of which is expressly incorporated into the present disclosure.

A presently preferred assembly for making the cover 64 is shown in FIGS. 3–6 and includes a 0.025 mm clear polyester film 66 (FIG. 3) covered by a printable mat topcoat ("Compucal II" brand, No. TC-329, Flexcon), an intermediate film 68 made either of a 0.13 mm polyester sheet having a metallized surface of aluminum bonded to the top film 66 or alternatively made of a 0.03 mm thick foil layer bonded to the top film 66, a high tack, non-repositionable 0.018–0.02 mm thick layer of acrylic pressure sensitive adhesive (No. H529, Flexcon), followed by a 0.025 mm thick polyester carrier film and a 0.018–0.02 mm (or optionally up to 0.05 mm) thick layer of low tack, repositionable acrylic pressure sensitive adhesive 70 (FIGS. 4–6) (No. H558, Flexcon). As an alternative to the carrier film and high and low tack adhesives set out above, one side of the carrier film may be first coated with a release agent, and then both sides may be covered with a high tack pressure sensitive acrylic adhesive (No. 300, 3M Company).

The films 66, 68 extend the full length and width of the cover 64, and the non-repositionable adhesive, the carrier film and the repositionable adhesive 70 are die cut to form an oval and an adjacent endmost rectangular section. The central portion of the oval is removed and matches the shape of the well 45, such that the repositionable adhesive 70 contacts only the top flange 44 and does not extend across the well 45; rather, the well 45 when closed by the cover 64 is covered by an exposed portion of the intermediate film 68.

The cover 64 has a line of perforations 65 that defines a rear hinge portion. Good results have been observed when the cover 64 has an overall width of 1.8 cm, and is provided with two perforations of 0.55±0.01 cm each and two perforations of 0.25±0.01 cm each, presentings three lands of 0.06±0.01 cm each, so that the ratio of total perforation length to land length is about 9 to 1. The perforations extend completely through the cover 64.

Figure 5:
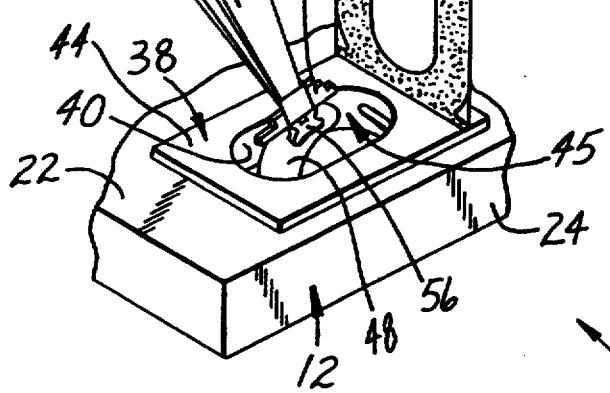
FIG. 5 is a view somewhat similar to FIG. 4 except that the cover is fully opened and a placement instrument has been inserted in a well of the container to grasp and remove an orthodontic bracket from the well.
Figure 6:
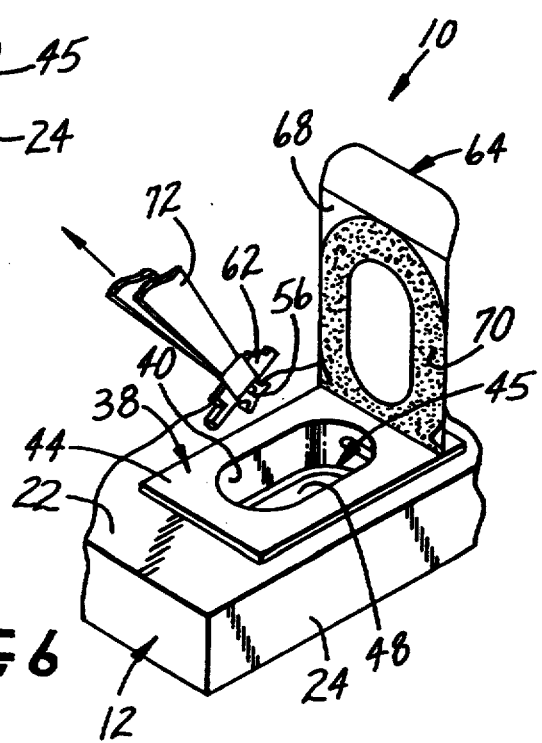
FIG. 6 is a view somewhat similar to FIG. 5 except that the bracket has been released from a flexible film secured to the well.

A front, inclined tab is formed for grasping the cover 64. When the tab of the cover 64 is grasped and pulled away from the carrier 22 in the direction of the arrow in FIG. 4, the cover 64 is moved to an open, upstanding position as shown in FIGS. 5, 6 and 8, bent at the rear line of perforations 65. The perforations 65 facilitate self-retention of the cover 64 in its open, upright position and permit the cover 64 to be made of relatively stiff materials. The perforations also provide tactile feedback to the user that the cover 64 is open so that the user does not continue to pull on the cover 64 and separate the latter from the carrier 22. As a result, the cover 64 along with any product identification information printed on the cover 64 is retained on the carrier 22 for future reference if needed, and the orthodontist need not dispose of a loose cover when the container 38 is opened.

The appliance 56 is firmly pressed onto the film 48 to ensure full facial contact of the adhesive 60 with the first section 52, but without force sufficient to extrude the adhesive 60 laterally from the exterior surface 58. When the cover 64 is closed, the top of the long axis indicator 62 is slightly spaced from the intermediate film 68 of the cover 64 as shown in FIG. 7. (As an alternative, the substrate 42 may have a central raised platform to decrease the space between the appliance 56 and the cover 64 when the indicator 62 is not provided).

In use, the cover 64 is opened when desired and a placement instrument 72 as shown in FIG. 5 is placed in the well 45 to grasp the sides of the appliance 56 or the sides of the indicator 62. Next, the instrument 72 is withdrawn from the well 45 in the direction of the arrows shown in FIGS. 5 and 6 until the appliance 56 with the adhesive 60 is released from the film 48. The appliance 56 is then placed on the patient's tooth, and a source of light is activated to cure the adhesive 60.

As the appliance 56 is lifted from the well 45, the first section 52 of the film 48 moves away from the substrate 42 while the second section 54 remains fixed to the substrate 42, causing the film 48 to assume a somewhat S-shaped configuration in reverse as shown in FIG. 8. Continued movement of the appliance 56 away from the Substrate 42 peels the first section 52 away from the adhesive 60 such that separation between the adhesive 60 and the first section 52 substantially occurs along a line or narrow band that advances toward the left-hand side of FIG. 8. In this manner, only a relatively small area of the adhesive 60 is directly adjacent the separating surfaces at any one time. The peeling effect facilitates separation of the adhesive 60 from the film 48 while leaving the adhesive 60 substantially undisturbed and in contact with the exterior surface 58 of the appliance 56.

Preferably, the distance of separation denoted A in FIG. 7 between the appliance 56 (and the first section 52) and the pressure sensitive adhesive 50 (and the second section 54) is as large as practical so that the appliance 56 may be lifted a sufficient distance from the well 45 to facilitate peeling of the film 48 in a direction generally perpendicular to the plane of the exterior surface 58. Additionally, the second section 54 of the film 48 together with the pressure sensitive adhesive 50 are preferably located toward the front of the box 12 (i.e., next to the slots 18 and facing in a direction away from the location where the lid 14 is hinged to the box 12) to facilitate the peeling effect. The oval-shaped configuration of the film 48 lacks corners which might otherwise contact the sidewall 40 and hinder lifting of the first section 52.

The separate containers 38 in combination with the carrier 22 are advantageous during manufacture because different containers, each holding a bracket for a different tooth, can be assembled in a single kit for a particular patient in accordance with the orthodontist's prescription. Further, individual containers allow the orthodontist to open only those containers that are presently needed, so that the adhesive on the remaining brackets is not unduly exposed to light, oxygen or water vapor.

A second embodiment of the invention is shown in FIGS. 9-10 wherein numerals in the drawings of a container 138 refer to elements that are the same as like-numbered elements described above in connection with the container 38 shown in FIGS. 1-8. However, in FIGS. 9-10, an oval-shaped bottom substrate 142 that is integrally connected to the sidewall 40 has a raised annular ridge 143 that provides a support for the overlying first section 52 of the film 48 in an orientation spaced slightly above the bottom of the well 45.

It has been found in connection with the embodiment shown in FIGS. 1-8 that as the appliance 56 is lifted from the well 45, the first section 52 of the film 48 occasionally clings to the underlying portion of the substrate 42 with such an affinity that the first section 52 resists lifting, with the result that the peeling effect shown in FIG. 8 does not occur and the adhesive 60 is instead detached from the appliance 56. While not a frequent problem, any inadvertent detachment of the adhesive 60 from the appliance 56 is a nuisance that is best avoided.

It is suspected that the silicone release agent on the container 38 wets the lower side of the film 48 and causes the first section 52 to cling to the substrate 42. Unfortunately, etching the film 48 as described earlier to enhance the bond to the adhesive 50 likely enhances the wetting of the film 48 with the silicone release agent. Unintentional detachment of the adhesive 60 has been observed to occur more often when the appliance 56 is metal rather than ceramic.

In FIGS. 9-10, the ridge 143 supports the first section 52 in such an orientation that full, planar, face-to-face contact with an underlying portion 147 of the substrate 142 is avoided and the total area of contact between the section 52 and the portion 147 is less than would be observed, for example, in connection with the embodiment shown in FIGS. 1-8. As a consequence, separation of the substrate 142 from the film 48 is facilitated when the appliance 56 is lifted from the well 45 so that the adhesive 60 routinely detaches from the film 48 in due course rather than detaching from the appliance 56.

The circular ridge 143 is located in a position centered directly beneath the exterior base surface 58 of the appliance 56. The area of the base surface 58 varies in accordance with the type and size of the appliance 56, but in general the area of the surface 58 is approximately equal to the area circumscribed by the ridge 143. As such, the ridge 143 extends along a path roughly following the perimeter of the surface 58.

Although the ridge 143 is shown for exemplary purposes as a currently preferred construction for reducing surface contact area between the substrate 142 and the film 48, it is to be understood in this regard that other constructions are also feasible and within the scope of the invention. For example, other shapes of ridges or shapes such as pyramids, peaks or bumps, continuous or broken, could be provided, preferably as the substrate 142 is molded. Ridges could be provided by numbers or letters formed in the substrate and the numbers or letters could be varied to provide identification of the manufacturing lot in order to facilitate tracing of the article after production. Reduction of contact area between the substrate 142 and the film 48 could alternatively be provided by altering the microstructure rather than the macrostructure of the substrate 142. For example, the substrate 142 could be scribed, scuffed or otherwise roughened, either by hand or by a rubberized grinding bit, to alter its pristine relatively smooth upper surface. In addition, alteration of either the microstructure or the macrostructure of the substrate 142 would be advantageous in circumstances where other phenomenon such as electrostatic attraction rather than mutually wetted surfaces tend to retain the film 48 in contact with the substrate 142.

We claim:

1. A dental packaging assembly comprising:
   a carrier having edge structure defining a plurality of openings;
   a plurality of containers each received in a respective one of said openings, each container having a top flange extending beyond the respective opening, a bottom defining a well and a sidewall extending between said top flange and said bottom;
   a dental appliance received in each of said wells; and
   a plurality of covers for initially closing said well of each respective container, each cover extending beyond the respective opening and releasably connected directly to said flange of the respective container,
   said sidewall of each container including a recess in contact with said edge structure for retaining said container in said opening.

2. The assembly of claim 1 including means for releasably retaining said container in said opening.

3. The assembly of claim 2, wherein said means comprises a flexible structure that includes said edge structure.

4. The assembly of claim 1, wherein said recess extends in a direction toward said well and is spaced from said flange.

5. The assembly of claim 1, and including a repositionable adhesive connected to said flange for selectively opening or closing said cover.

6. The assembly of claim 1, including an adhesive on each appliance, and a flexible film connected to each container, wherein said film includes a low adhesion surface in contact with said adhesive.

7. The assembly of claim 6, wherein said film has a first section and a second section spaced from said first section, said second section being connected to said container and said first section being in contact with said adhesive.

* * * * *

UNITED STATES PATENT AND TRADEMARK OFFICE
CERTIFICATE OF CORRECTION

PATENT NO. : 5,429,229
DATED : July 4, 1995
INVENTOR(S) : Bruce E. Chester, Kenneth E. Hoevel and Dwight W. Jacobs It is certified that error appears in the above-indentified patent and that said Letters Patent is hereby corrected as shown below:

Item [[75]],
On the cover page, please delete the names Lawrence G. Brusby and Evangelos G. Georgakis as inventors.

Col. 3 line 35, insert -- 22 -- after "carrier".

Col. 6, line 60, "Substrate" should read -- substrate --.

Signed and Sealed this

Twenty-sixth Day of September, 1995

Attest:

BRUCE LEHMAN

Attesting Officer      *Commissioner of Patents and Trademarks*